(12) United States Patent
Saltykov

(10) Patent No.: US 6,860,362 B2
(45) Date of Patent: Mar. 1, 2005

(54) HEARING AID INSTRUMENT FLEXIBLE ATTACHMENT

(75) Inventor: Oleg Saltykov, Fairlawn, NJ (US)

(73) Assignee: Siemens Hearing Instruments, Inc., Piscataway, NJ (US)

( * ) Notice: Subject to any disclaimer, the term of this patent is extended or adjusted under 35 U.S.C. 154(b) by 93 days.

(21) Appl. No.: 10/371,115

(22) Filed: Feb. 21, 2003

(65) Prior Publication Data
US 2003/0178247 A1 Sep. 25, 2003

Related U.S. Application Data

(60) Provisional application No. 60/365,945, filed on Mar. 20, 2002.

(51) Int. Cl.⁷ .............................................. A61B 7/02
(52) U.S. Cl. ...................... 181/135; 181/129; 181/130; 181/134; 381/328
(58) Field of Search ................................ 181/135, 129, 181/130, 134; 381/328

(56) References Cited

U.S. PATENT DOCUMENTS

| | | | |
|---|---|---|---|
| 2,142,407 A | * | 1/1939 | Norton et al. .............. 181/135 |
| 2,803,308 A | | 8/1957 | Di Mattia |
| 4,607,720 A | | 8/1986 | Hardt .......................... 181/130 |
| 4,880,076 A | | 11/1989 | Ahlberg et al. .............. 181/130 |
| 5,002,151 A | | 3/1991 | Oliveira et al. ............. 181/130 |
| 5,031,219 A | | 7/1991 | Ward et al. .................. 381/328 |
| 5,201,007 A | | 4/1993 | Ward et al. .................. 381/328 |
| 5,362,180 A | * | 11/1994 | Canning et al. .............. 405/66 |
| 5,742,692 A | | 4/1998 | Garcia et al. ............... 381/328 |
| 5,748,743 A | | 5/1998 | Weeks ......................... 381/328 |
| 5,881,159 A | | 3/1999 | Aceti et al. ................. 381/328 |
| 5,979,589 A | | 11/1999 | Aceti .......................... 181/135 |
| 6,129,174 A | | 10/2000 | Brown et al. ............... 181/135 |
| 6,253,871 B1 | | 7/2001 | Aceti .......................... 181/135 |
| 6,349,790 B1 | * | 2/2002 | Brimhall ..................... 181/135 |

OTHER PUBLICATIONS

Songbird Digital technology http://www.songbirdhearing.com/professionals/product/product.asp Picture of the songbird Tip advertised around 1999.

* cited by examiner

*Primary Examiner*—Shih-yung Hsieh
(74) *Attorney, Agent, or Firm*—Alexander J. Burke; Joel Miller

(57) ABSTRACT

A flexible device having a flexible cup for attachment to a hearing aid housing for insertion in an ear canal of a user. The flexible cup includes an opening for securely accommodating a hearing aid housing upon insertion of the housing in the opening. The flexible cup also includes a plurality of spiral shaped ribs on an inner surface of the cup.

19 Claims, 7 Drawing Sheets

HEARING AID INSTRUMENT FLEXIBLE ATTACHMENT

This is a non-provisional application based on provisional patent application Ser. No. 60/365,945 filed Mar. 20, 2002.

BACKGROUND OF THE INVENTION

1. Field of the Invention

The present invention relates generally to hearing aids and, more specifically, to ear pieces for retaining a microphone within an ear canal of a user.

2. Description of the Prior Art

Numerous types ear pieces are known in the prior art. Ear pieces are generally used to hold a microphone of a hearing aid within the ear canal of a user. It is important to provide an ear piece that fits comfortably within the ear canal of a user and also functions to prevent sound from leaking out from the ear canal. Prior art ear pieces are generally cylindrical in shape. Such prior art ear pieces have encountered the problem of collapsing when inserted in the ear. In order to reduce the occurrence of collapse, ear pieces were provided with ribs to provide additional stability to the ear piece. In order to prevent collapse, ear pieces were provided with circular ribs extending around a circumference thereof or straight ribs extending along a length of an inner side of the ear piece. The addition of these styles of ribs improved the ear pieces. However, such ear pieces were not completely effective and still allowed for at least a portion of the ear piece to collapse when placed inside the ear canal of a user. As these prior art ear pieces were subject to total or partial collapse, they were not able to fully retain sound inside the ear canal thereby causing a user to experience feedback when the sound leaking from the ear canal into the area containing the microphone.

SUMMARY OF THE PRESENT INVENTION

A flexible device having a flexible cup for attachment to a hearing aid housing for insertion in an ear canal of a user. The flexible cup includes an opening for securely accommodating a hearing aid housing upon insertion of the housing in the opening. The flexible cup also includes a plurality of spiral shaped ribs on an inner surface of the cup.

BRIEF DESCRIPTION OF THE DRAWING FIGURES

In order that the invention may be more fully understood, it will now be described, by way of example, with reference to the accompanying drawing in which.

Figure 3:
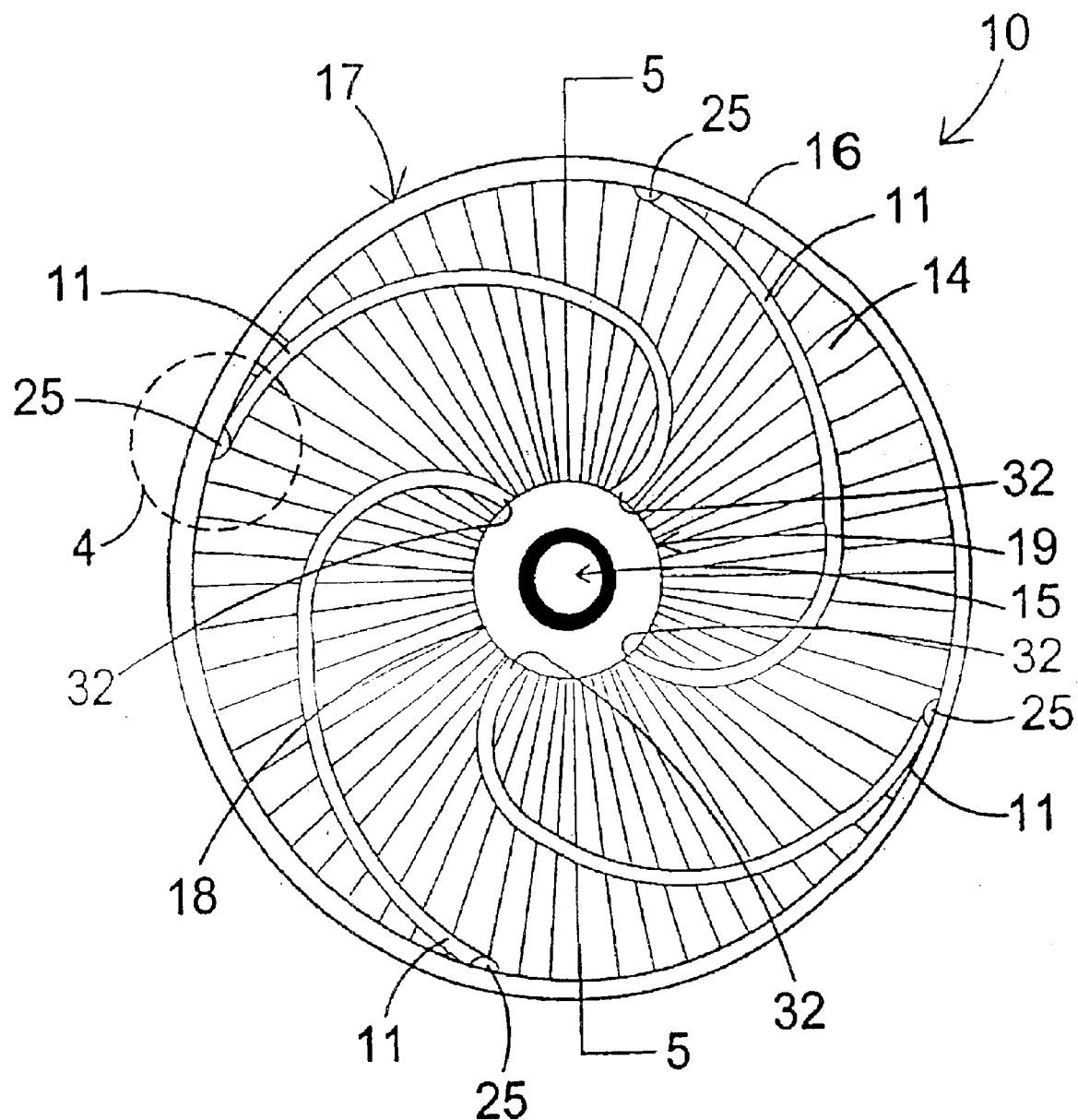
Figure 4:
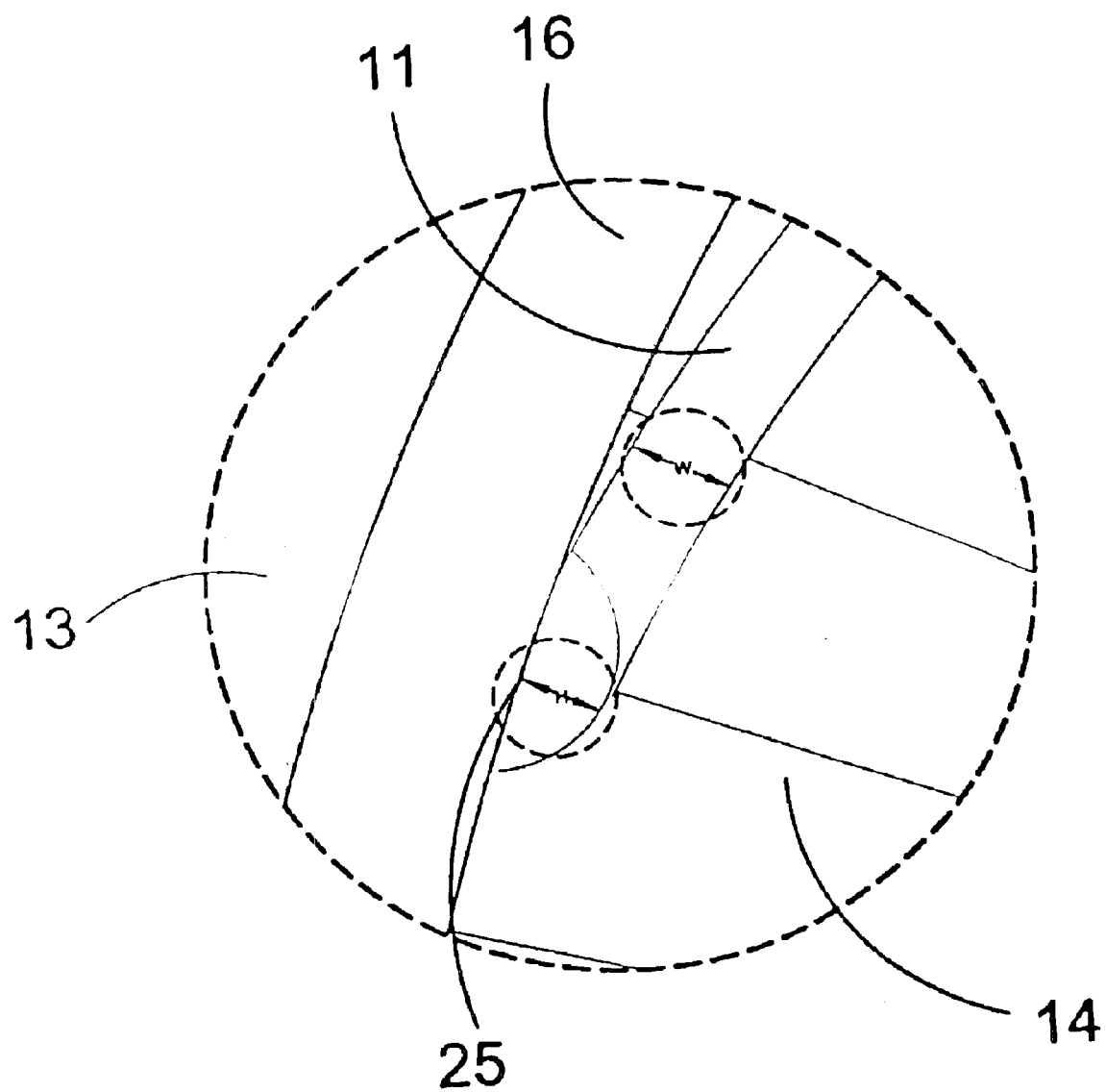
Figure 5:
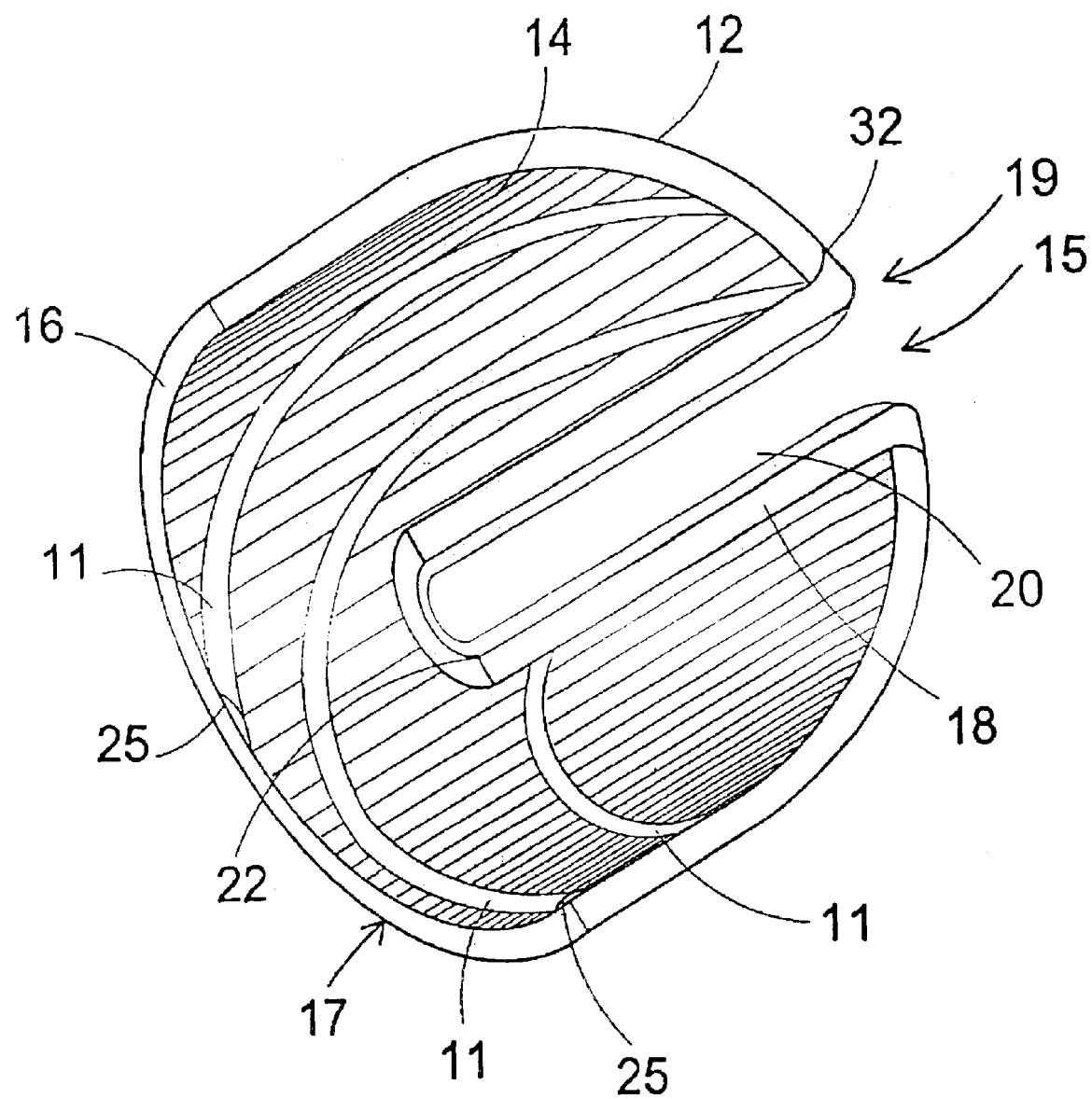
Figure 6:
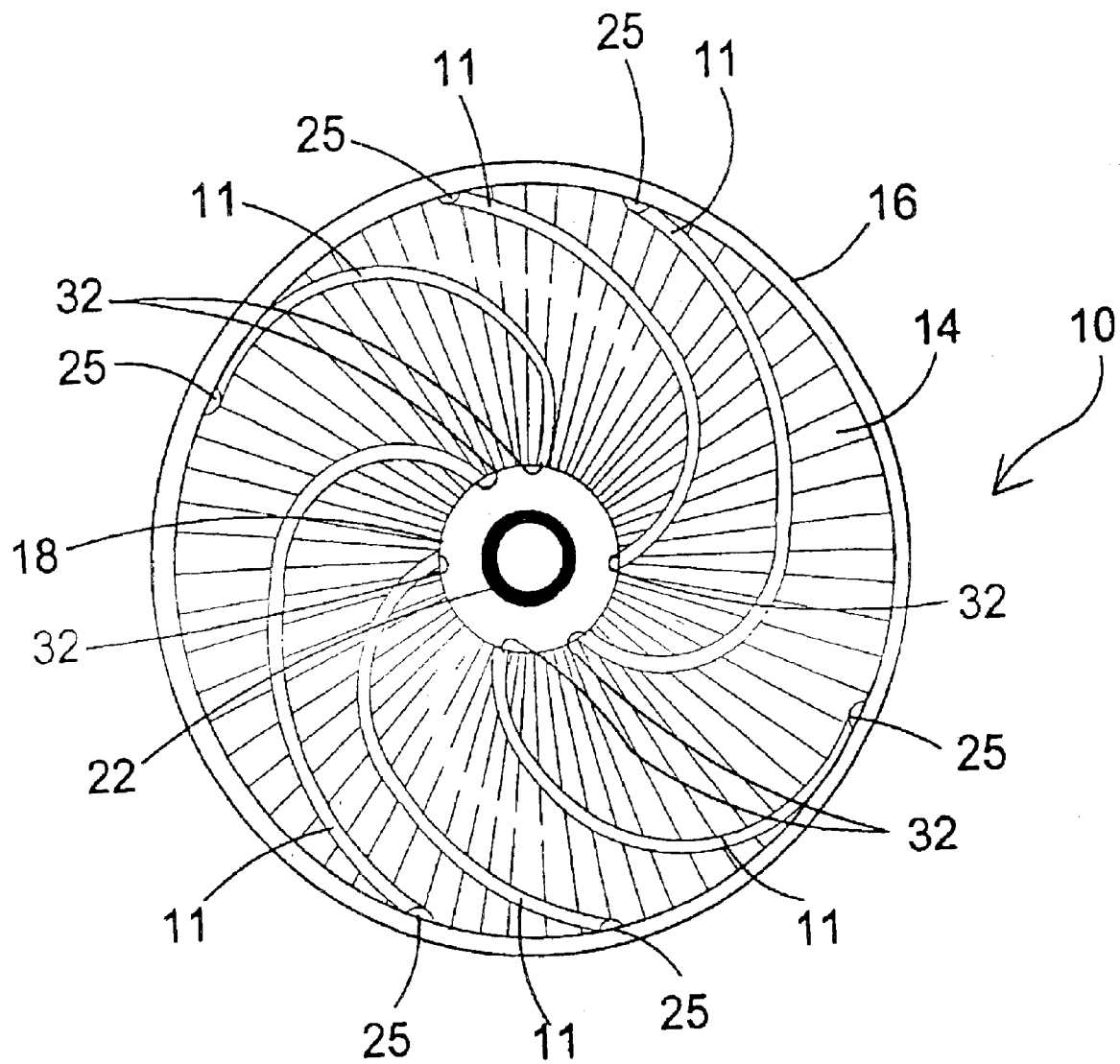
Figure 7:
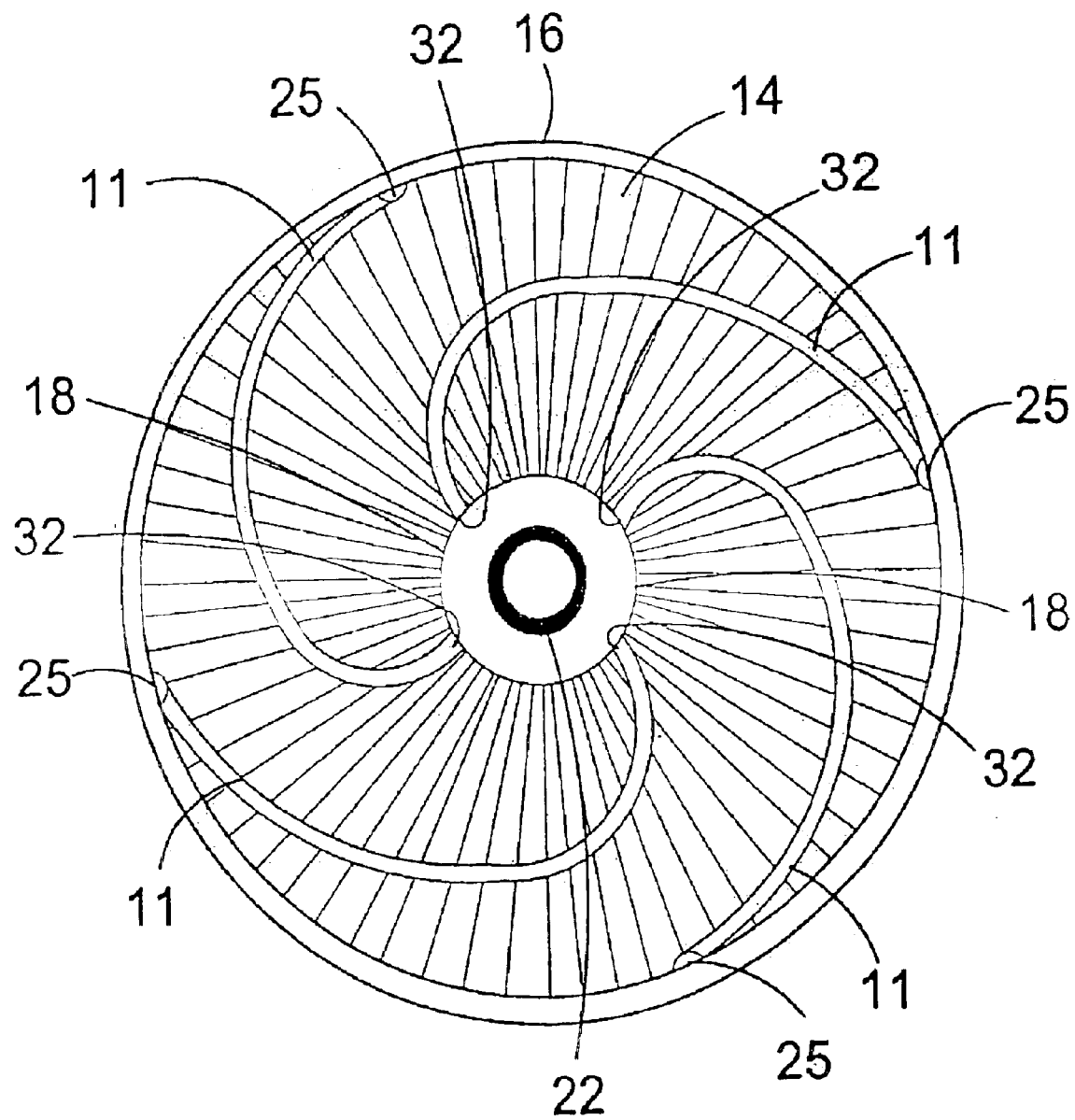

FIG. 3 a front view of the ear piece of the present invention having a plurality of spiral ribs;

FIG. 4 is a cutaway view of the origin point of a spiral rib along an edge of the ear piece of the present invention taken within the circle labeled 4 in FIG. 3;

FIG. 5 is a cross-sectional view of the ear piece of the present invention taken along line 5—5 in FIG. 3;

FIG. 6 is a front view of the ear piece of the present invention having an additional number of spiral ribs; and FIG. 7 is a front view of the ear piece of the present invention having ribs that spiral in a counterclockwise direction.

The foregoing and other objects and advantages will appear from the description to follow. In the description, reference is made to the accompanying drawing, which forms a part hereof, and in which is shown by way of illustration specific embodiments in which the invention may be practiced. These embodiments will be described in sufficient detail to those skilled in the art to practice the invention, and it is to be understood that other embodiments may be utilized and that structural changes may be made without departing from the scope of. In the accompanying drawings, like reference characters designate the same or similar parts throughout the several views

DETAILED DESCRIPTION OF THE PREFERRED EMBODIMENTS

The following discussion describes in detail one embodiment of the invention and several variations of that embodiment. This discussion should not be construed, however, as limiting the invention to those particular embodiments. Practitioners skilled in the art will recognize numerous other embodiments as well. For a definition of the complete scope of the invention, the reader is directed to the appended claims.

Turning now descriptively to the drawings, in which similar reference characters denote similar elements throughout the several views. FIGS. 1 through 7 illustrate the ear piece of the present invention indicated generally by the numeral 10.

Figure 1:
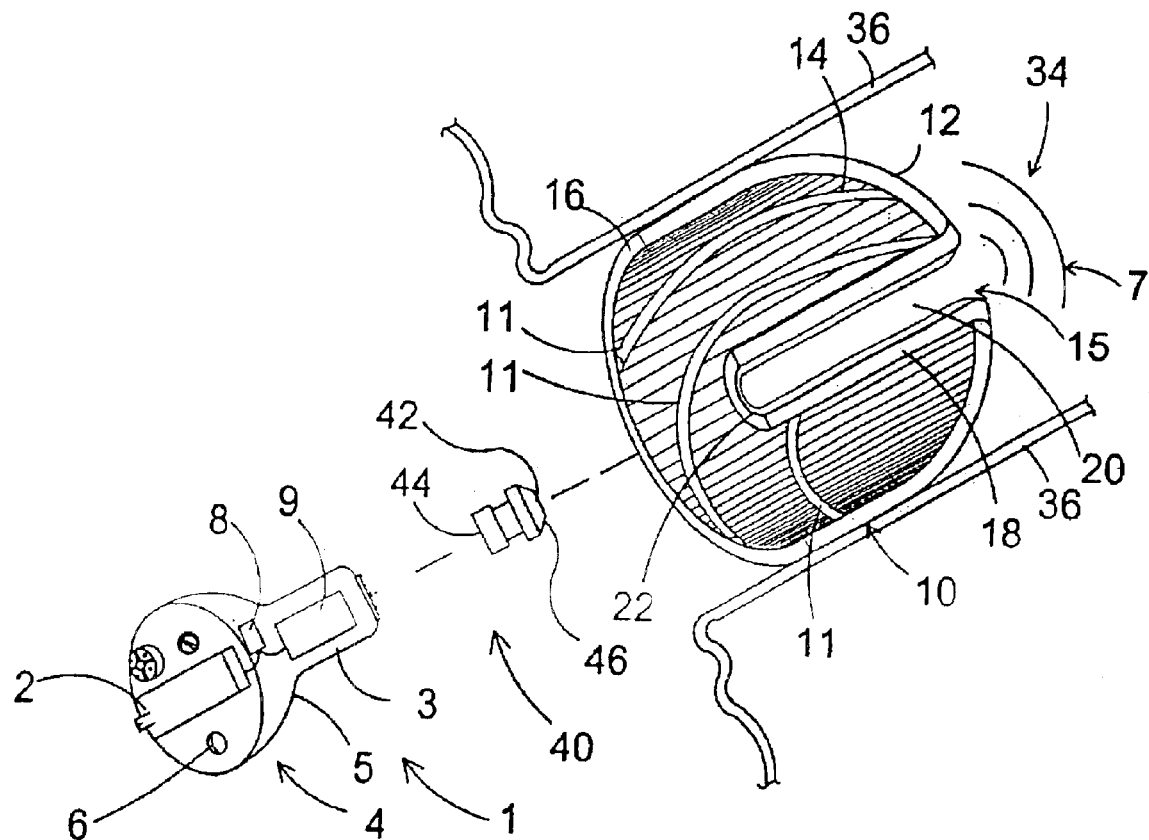
FIG. 1 is an exploded cross-sectional view of a hearing aid positioned within an ear canal and including the ear piece of the present invention having a plurality of spiral ribs retained within an ear canal of a user.

FIG. 1 is an exploded cross-sectional view of a hearing aid 1 positioned within an ear canal 34 and including the ear piece 10 of the present invention. As can be seen from this Figure, the ear piece 10 includes a dome shaped housing 12 with a plurality of spiral ribs 11 extending around an interior surface 14 thereof. The ear piece 10 is shown retained within the ear canal 34 of a user. The ear piece 10 has an exterior surface opposite the interior surface 14 and contacting a surface 36 of the ear canal 34. The dome shaped housing 12 further includes an edge 16 extending around one end thereof between the interior surface 14 and an exterior surface 13, the exterior surface 13 is clearly shown in FIG. 2. The interior surface 14 of the dome shaped housing 12 forms a cup. At a base of the cup is a channel 15 extending through a central section the dome shaped housing. A cylinder 18 is located within the cup and extending from the channel 15 of the dome shaped housing 12. The cylinder 18 is preferably integrally formed with the housing 12 and is able to receive and retain a hearing aid module 4 therein via an adapter 40. The cylinder 18 has a beveled edge 22 on a side opposite the connection with the housing 12. The beveled edge 22 assists in retaining the adapter 40 within the cylinder 18.

The hearing aid module 4 includes a custom shell 5 made to uniquely fit the shape of the ear canal 34 of the user. The module 4 further includes a microphone 6, a circuit 8, a receiver 9, and power source 2 for providing power thereto. The circuit 8 is electrically connected to both the microphone 6 and the receiver 9. The receiver 9 is connected within a tube 3 of the shell 5. The microphone 6 receives sounds from an external source and converts the received sound signal into an electrical signal. The circuit 8 amplifies the signal as received by the microphone 6. Thereafter, the receiver 9 processes and converts the amplified electrical signal from the circuit 8 back into a sound signal and the sound signal passes through the tube 3 into the adapter 40, and further through the cylinder 18 of the ear piece 10 where the sound signal is ultimately received by the ear canal 34.

The adapter 40, which connects the module 4 to the cylinder 18 of the ear piece 10, is preferably cylindrical in shape. The adapter 40 includes an axially located channel 42 extending through the center for passing the sound signal from the hearing aid module 4 into the ear. The adapter 40 further includes a first end 44 which connects to the tube 3 of the module 4. Preferably the tube 3 is screwed into the first end 44 of the adapter 40. However, any means to connect the module 4 to the first end 44 of the adapter 40 may be used. The adapter 40 also includes a second end 46 located opposite the first end 44. The second end 46 connects the adapter 40 to the cylinder 18 of the ear piece 10. Preferably, the second end 46 is beveled so as to fit securely within the beveled edge 22 of the cylinder 18. However, the second end 46 of the adapter can be formed in any way such as to provide a secure connection between the adapter 40 and the cylinder 18.

The plurality of spiral ribs 11 of the ear piece 10 are positioned on and extend around the interior surface 14 of the dome shaped housing 12. The spiral ribs 11 spiral from the edge 16 into the center of the cup of the dome shaped housing 12 providing support over the entire surface of the dome shaped housing 12.

As shown in FIG. 1, the dome shaped housing 12 fits securely within the ear canal 34 of a user. The plurality of spiral ribs 111 add rigidity to the dome shape housing 12 and cause the housing 12 to remain in contact with the surface 36 of the ear canal 34. The plurality of spiral ribs 11 cause a tight seal to be created between the ear piece 10 and the surface 36 of the ear canal 34 thereby preventing collapse of the housing 12 and preventing gaps from forming between the edge 16 of the ear piece 10 and the surface 36 of the ear canal 34. When the hearing aid module 4 is received by the cylinder 18, it is able to pick up external sounds and transfer the received sounds through the cylinder 18 and into the ear canal 34, as discussed above. The sound is represented by the arrow labeled 7. The tight seal created between the surface 36 of the ear canal 34, and the ear piece 10 prevents sound 7 from leaking back into the outer ear where the microphone 6 is located and thereby minimizing feedback.

Figure 2:
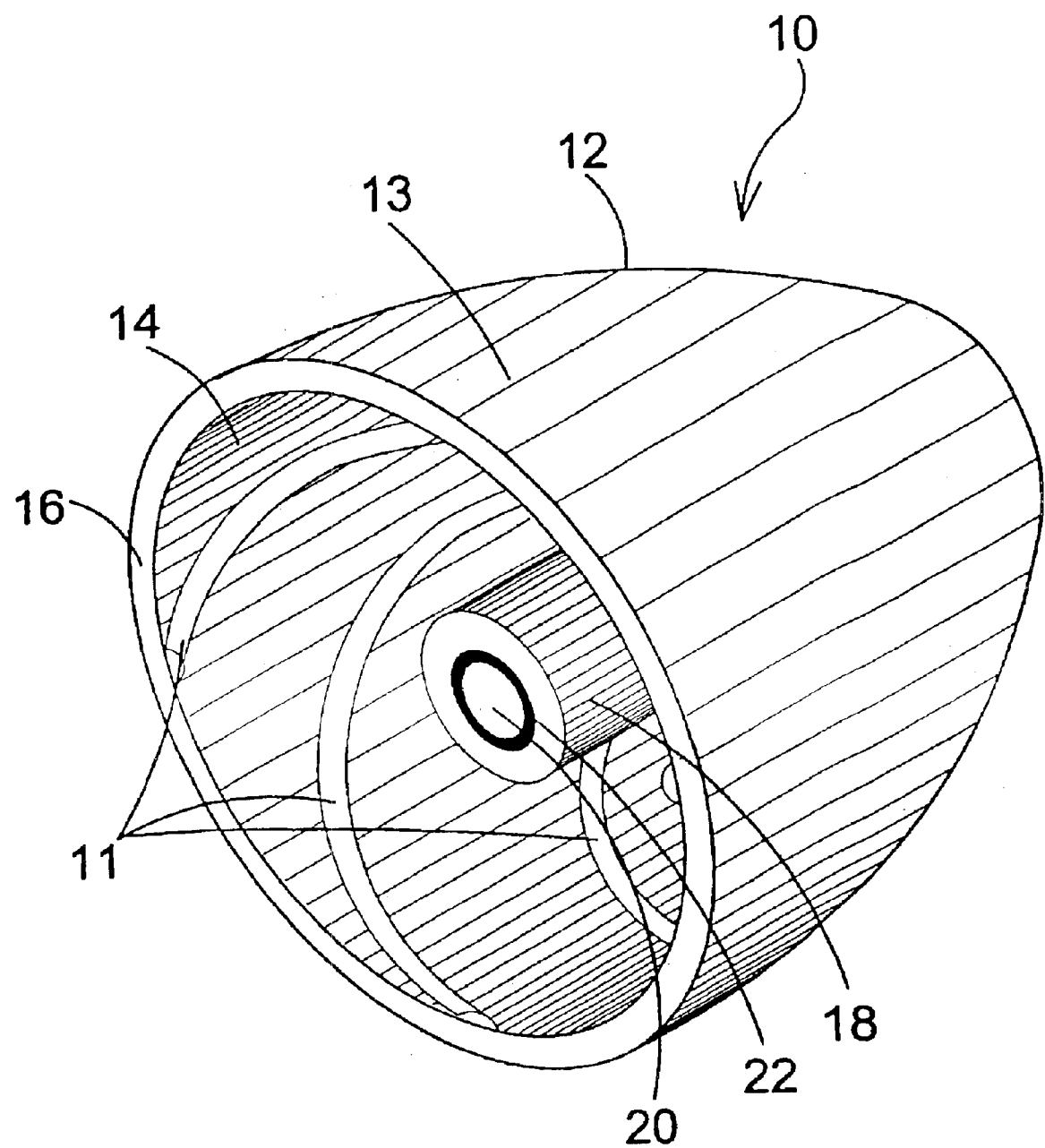
FIG. 2 is a perspective view of the ear piece of the present invention having a plurality of spiral ribs.

FIG. 2 is a perspective view of the ear piece 10 of the present invention having a plurality of spiral ribs 11. The ear piece 10 of the present invention includes the dome-shaped housing 12 for receipt by the ear canal of the user as can be seen in FIG. 1. The housing 12 includes the exterior surface 13 and interior surface 14 which form the cup. Extending upward from substantially the center of the cup of the interior is the cylinder 18. The cylinder 18 has the inner surface 20 which receives the adapter of the hearing aid module. The beveled edge 22 is located on the side of the cylinder 18 opposite the connection to the housing 12 and aides in retaining the adapter of the hearing aid module within the cylinder by allowing the adapter to be snap fit into the cylinder 18. The use of a beveled edge 22 for securing the adapter of the hearing aid module into position is described for purposes of example only. In practice, any means by which the adapter can be held into place within the cylinder 18 may be used. Upon connection of the adapter to the cylinder 18, a channel is formed which allows sound to pass from the microphone of the hearing aid through the adapter and further through the cylinder 18 into the ear of the user.

The ear piece 10 further includes spiral ribs 11 spiraling along the interior surface 14 of the housing 12. The spiral ribs 11 extend along the interior surface 14 of the housing 12 between the edge 16 of the housing 12 and the connection point of the cylinder 18 to the housing 12. The spiral ribs 11 protrude to a predetermined height from the interior surface 14. Preferably the interior surface 14 of the housing 12 contains a plurality of spiral ribs extending spirally along the interior surface 14 thereof. However, in practice any number of spiral ribs may extend along the length of the interior surface 14. Each of the spiral ribs 11 extend from a different position along a circumference of the edge 16 of the housing 12, and terminate at a different point around the cylinder 18. As shown in this figure, the spiral ribs 11, spiral in a clockwise direction along the interior surface 14 of the housing 12 and provide support for the housing 12 of the ear piece 10. Alternatively, as shown in FIG. 6 and discussed hereinafter the spiral ribs may spiral in a counterclockwise direction. The direction in which the ribs spiral does not affect the ability of the ribs to provide support for the ear piece and prevent collapsing.

FIG. 3 is a front view of the ear piece 10 of the present invention having a plurality of spiral ribs 11. As can be seen from this Figure the interior surface forms the cup which has a circular first end 17 and a second end 19 including a channel 15 at a side opposite the first end 17. Extending into the cup at substantially the point of the channel 15 is the cylinder 18. The cylinder 18 has the beveled edge 22 for aiding in retaining of the adapter of the hearing aid module for receiving sound from an external source and transmitting that sound to the user via the user's ear canal. The spiral ribs 11 extend along the interior surface 14 between a respective origin point 25 positioned along the circumference of the edge 16 and a respective termination point 32 positioned around the cylinder 18 at the connection of the cylinder 18 to the interior surface 14. The origin points 25 of each rib 11 are preferably positioned at equal intervals along the circumference of the edge 16. Likewise, each of the termination points 32 are preferably positioned at equal intervals around the cylinder 18. The number of ribs spiraling along the length of the interior surface 14 is determined by the distance between the origin and termination points.

The number of spiral ribs 11 extending along the interior surface 14 of the housing 12 correlates to the strength and support provided by the ribs 11 of the ear piece 10. Preferably the ribs 11 extend at substantially similar arcs along the interior surface. Having substantially the same degree of arc allows for the ribs 11 to provide maximum support and stability over the entire interior surface 14 of the housing 12 thereby preventing any collapse from occurring, and forming a tight seal when the ear piece 10 is inserted into an ear canal of a user. However, the arc at which the ribs 11 extend may differ and the ribs 11 may even cross one another as they extend along the interior surface 14.

FIG. 4 is a cutaway view of the origin point 25 of a spiral rib 11 along an edge of the ear piece 10. Herein, the rib 11 is shown at its origin point 25 along the edge 16 of the housing 12. The rib 11 protrudes from the interior surface 14 of the housing 12 at a predetermined height H. The height H is dependent upon the amount of stability desired and the rigidity of the material used in manufacture of the ear piece. However, regardless of the type of plastic used in manufacture of the ear piece 12, the ribs 11 should protrude a distance to provide a sufficient amount of structure and support to prevent collapsing of the housing 12 upon and after insertion into a user's ear canal. The rib 11 also has a width W. The width W of the rib 11 also is dependent upon the amount of stability desired and the rigidity of the material used in the manufacture of the ear piece 10. The width W of the rib 11 can vary along the length thereof whereby, for example, a rib may have a larger width at points along the rib 11 closer to the origin point 25 and the termination point, and a smaller W along the rib 11 between the origin point 25 and the termination point. The materials used in the manufacture of the ear piece include at least one of plastic, rubber, compounds, composites, and aggregates. However, any other composition providing flexibility and compatibility with human skin may be used in the manufacture of the ear piece 10 of the present invention.

FIG. 5 is a cross-sectional view of the ear piece 10 of the present invention taken along line 5—5 in FIG. 3. The interior surface of the housing 12 is shown in this Figure. The edge 16 of the housing extends circularly around the first end 17 of the housing 12. The interior surface 14 of the dome shaped housing 12 forms a cup therein with the second end 19 acting as the base of the cup. The channel 15 extends through the second end 19. The cylinder 18 is located at and extends upwardly from the second end 19 of the dome shaped housing 12 and is positioned in alignment with the channel 15. The cylinder 18 includes an inner surface 20 having a circumference substantially equal to a circumference of the channel 15. The adapter of a hearing aid module is received within the cylinder 18 and held against the inner surface 20. The cylinder 18 also has the beveled edge 22. The beveled edge 22 aides in retaining the adapter within the cylinder 18. The beveled edge 22 allows the adapter to snap into place.

As also can be seen from this figure the spiral ribs 11 begin at the first origin point 25 positioned on the edge 16 of the interior surface 14 and extend along the interior surface 14 to a termination point 32 along an outer surface of the cylinder 18. The spiral ribs 11 provide support over the entire interior surface 14 of the dome shaped housing 12 and prevent any unwanted collapse thereof.

FIG. 6 is a front view of the ear piece 10 of the present invention having six spiral ribs 11. This Figure is provided to illustrate that the earpiece of the present invention may include any desired number of spiral ribs 11. The number of spiral ribs 11 being dependent upon the desired amount of stability for the earpiece 10.

FIG. 7 is a front view of the ear piece of the present invention having ribs that spiral in a counterclockwise direction. This figure is provided to illustrate that the direction in which the ribs 11 spiral along the length of the interior surface does not affect the ability of the earpiece 10 of the present invention to resist collapse and is based upon the desires of the manufacturer.

The ear piece 10 of the present invention is preferably formed from a resilient plastic. The plastic which forms the ear piece 10 should be hypo-allergenic to prevent any allergic reaction when the ear piece 10 is inserted into the ear canal of a user. Further, the plastic used in manufacture of the ear piece 10 is preferably comfortable and pliable thereby allowing secure fitting into any ear canal. Further, the type of plastic used in the manufacture of the ear piece 10 determines the height at which the spiral ribs 11 extend along the interior surface as well as the thickness of the ribs 1. The positioning of the ribs 11 and number of ribs 11 along the interior surface of the housing 12 also is dependent upon the type of plastic used in the manufacture of the ear piece 10.

From the above description it can be seen that the present invention overcomes the shortcomings of the prior art by providing an ear piece for a hearing aid having a plurality of spiral ribs positioned along an interior surface of the ear piece for preventing collapse at any point on the ear piece while maintaining a comfortable fit within the ear canal of a user, and thereby preventing the leakage of sound pressure from the ear canal of a user back into the area where a microphone of a hearing aid receives incoming sound. Furthermore, the present invention is relatively simple and easy to manufacture and is customer friendly in fitting and use.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A flexible device for use with a hearing aid instrument for positioning in an ear of a user, comprising:
   a flexible cup for attachment to a hearing aid housing for insertion in an ear canal of a user, said flexible cup including:
   an opening for securely accommodating a hearing aid housing upon insertion of said housing in said opening, and
   a plurality of spiral shaped ribs on an inner surface of said cup.

2. The flexible device as recited in claim 1 wherein said flexible cup is a dome shaped housing having an interior surface, an exterior surface, an edge extending around an end of said housing and between said interior and exterior surfaces.

3. The flexible device as recited in claim 2 wherein said opening extends through said housing on a side opposite said edge.

4. The flexible device as recited in claim 3 further comprising a cylinder, said cylinder having a channel extending therethrough extends from said interior surface and said channel is aligned with said opening.

5. The flexible device as recited in claim 4 wherein said plurality of spiral ribs protrude from said interior surface and extend spirally along said interior surface substantially between said edge and said cylinder for supporting said housing.

6. The flexible device as recited in claim 5 wherein said plurality of ribs are equally spaced about said interior surface.

7. The flexible device as recited in claim 5 wherein said ear piece is formed from a resilient hypoallergenic plastic.

8. The flexible device as recited in claim 5 wherein each of said plurality of spiral ribs extend at a predetermined degree of arc.

9. The flexible device as recited in claim 8, wherein said predetermined degree of arc of said plurality of spiral ribs is substantially the same.

10. The flexible device as recited in claim 8, wherein said predetermined degree of arc of each of said plurality of spiral ribs is different.

11. The flexible device as recited in claim 5 wherein each of said plurality of spiral ribs has a predetermined thickness.

12. The flexible device as recited in claim 11 wherein said predetermined thickness of each of said plurality of spiral ribs is substantially the same.

13. The flexible device as recited in claim 11 wherein said predetermined thickness of each of said plurality of spiral ribs is different.

14. The flexible device as recited in claim 11 wherein said predetermined thickness varies along the length of each of said plurality of spiral ribs.

15. The flexible device as recited in claim 5 wherein said plurality of spiral ribs is at least four spiral ribs.

16. The flexible device as recited in claim 5 wherein said plurality of spiral ribs extend in a clockwise direction.

17. The flexible device as recited in claim 5 wherein said plurality of spiral ribs extend in a counterclockwise direction.

18. The flexible device as recited in claim 1 is manufactured from at least one of plastic, rubber, composites, compounds, aggregates, and any other material that is flexible and is compatible with human skin.

19. An ear piece for holding a microphone of a hearing aid comprising:
   a) a cup shaped housing having an interior surface, an exterior surface, an edge extending around an end of said housing and between said interior and exterior surfaces, and a channel extending through said housing on a side opposite said edge;
   b) a cylinder extending from said interior surface and aligned with said channel; and
   c) a spiral rib protruding from said interior surface and extending spirally along said interior surface substantially between said edge and said cylinder for supporting said housing when said ear piece is inserted into an ear canal of a user thereby preventing collapse of said housing and any feedback resulting therefrom.

* * * * *